United States Patent [19]
Theriot

[11] Patent Number: 5,068,487
[45] Date of Patent: Nov. 26, 1991

[54] OLEFIN OLIGOMERIZATION WITH BF$_3$ ALCOHOL ALKOXYLATE CO-CATALYSTS

[75] Inventor: Kevin J. Theriot, Baton Rouge, La.

[73] Assignee: Ethyl Corporation, Richmond, Va.

[21] Appl. No.: 554,727

[22] Filed: Jul. 19, 1990

[51] Int. Cl.$^5$ .............................................. C07C 2/04
[52] U.S. Cl. .................................... 585/510; 585/525
[58] Field of Search ...................... 585/510, 511, 525

[56] References Cited

U.S. PATENT DOCUMENTS

| | | | |
|---|---|---|---|
| 2,806,072 | 9/1957 | Cohen et al. | 260/683.15 |
| 3,382,291 | 5/1968 | Brennan | 260/683.15 |
| 4,172,855 | 10/1979 | Shubkin et al. | 585/16 |
| 4,218,330 | 8/1980 | Shubkin | 252/46.6 |
| 4,902,846 | 2/1990 | DiLeo et al. | 585/525 |

*Primary Examiner*—Curtis R. Davis
*Attorney, Agent, or Firm*—D. M. Bunnell

[57] ABSTRACT

A process for making an α-olefin oligomer comprises contacting an α-olefin monomer containing from about 6 to 20 carbon atoms with a catalyst comprising boron trifluoride and an alcohol alkoxylate so as to form an oligomer product.

21 Claims, No Drawings

OLEFIN OLIGOMERIZATION WITH BF₃ ALCOHOL ALKOXYLATE CO-CATALYSTS

BACKGROUND

This invention relates generally to the preparation of alpha-olefin oligomers which are useful as synthetic lubricants and functional fluids and more particularly to a $BF_3$-promoter catalyst system using alcohol alkoxylates as promoters to control the oligomer product distribution and especially to provide higher percentages of lower oligomers.

Alpha-olefin oligomers and their use as synthetic lubricants ("synlubes") are well-known. The oligomers are usually hydrogenated in order to improve their stability. Early reports of such synlubes are in Seger et al. U.S. Pat. No. 2,500,161 and Garwood U.S. Pat. No. 2,500,163. U.S. Pat. No. 2,766,312 describes the oligomerization of α-olefins in a Group IV metal oxide bed using a $BF_3$-polar promoter catalyst. Promoters include water, carboxylic acid, alkyl halides, alcohols and ethers. U.S. Pat. No. 2,806,072 discloses the dimerization of $C_6$-$C_{12}$ polypropylenes using a preformed $BF_3$-dialkylether catalyst. U.S. Pat. No. 3,882,291 describes the oligomerization of olefins using $BF_3$-promoter catalyst complexes which include acid anhydrides, esters, ketones and aldehydes. U.S. Pat. No. 4,172,855 describes $BF_3$-promoter catalysts for grafting a second α-olefin onto $C_6$-$C_{12}$ α-olefin dimer to form a low volatility lubricating oil. The promoters include glycol ethers such as ethylene glycol monomethyl ether, propylene glycol monoethyl ether, and di-isobutyl ether.

The particular applications for which the oligomer oils are used depends upon their viscosity, with viscosities of about 2-10 cSt at 100° C. being preferred for general lubricating oil applications. These materials are mixtures of different percentages of dimer, trimer, tetramer, pentamer and higher oligomers which oligomers are produced in different proportions in the oligomerization process. In order to increase the viscosity, processes are used which either produce more of the higher oligomers or some of the lower oligomers are removed such as by distillation. Most low viscosity dimer and trimer products are obtained as by-products of the production of higher viscosity synthetic oils. Due to the increasing use of dimers in applications such as low temperature lubricants and drilling fluids, methods for their preferential production are of interest. It is known that higher temperatures favor dimer production, but such higher temperatures can cause corrosion of production equipment. I have now discovered a new process for producing dimers as the primary oligomerization product at moderate temperatures.

BRIEF SUMMARY

In accordance with this invention, there is provided a process for making a o-olefin oligomer comprising contacting an α-olefin monomer containing from about 6 to 20 carbon atoms with a catalyst comprising boron trifluoride and alcohol alkoxylate so as to form an oligomer product.

In one embodiment of the invention the co-catalyst complex is recycled.

DETAILED DESCRIPTION

The olefins used in making the oligomer are predominately (at least 50 mole percent) $C_6$ to $C_{20}$ straight-chain monoolefinically unsaturated hydrocarbons in which the olefinic unsaturation occurs at the 1- or alpha-position of the straight carbon chain. Such alpha-olefins are commercially available and can be made by the thermal cracking of paraffinic hydrocarbons or by the well-known Ziegler ethylene chain growth and displacement on triethyl aluminum. Individual olefins may be used as well as mixtures of such olefins. Examples of such olefins are 1-hexene, 1-heptene, 1-octene, 1-nonene, 1-decene, 1-dodeoene, 1-hexadecene and 1-tetradecene. The more preferred normal-alpha-olefin monomers are those containing about 8-12 carbon atoms. The most preferred olefin monomer is 1-decene.

The olefin monomers can also contain minor amounts of up to about 50 and usually less than 25 mole percent of internal olefins and vinylidene olefins.

The olefin is contacted as known in the art with a catalytic amount of boron trifluoride which should be at least about 0.002 moles per mole of olefin. Preferably the reaction mixture is saturated with $BF_3$. To be effective, the boron trifluoride is used in combination with a promoter which is an alcohol alkoxylate. This promoter surprisingly favors the production of lower oligomers and particularly products containing predominantly dimer and trimer with a dimer to trimer ratio of greater than about 1. Under ordinary reaction conditions the dimer does not further react, and particularly does not dimerize, to any significant extent so that the reaction is easily controllable to produce a large proportion (at least about 40 and preferably 50 to 85 wt % or more dimer based on the total weight of oligomers in the product) of dimer. The dimer content asymptotically approaches a maximum rather than sharply peaking at a transient maximum, which is common in prior processes.

Alcohol alkoxylates useful in the invention can be represented, for example, by the formula:

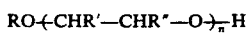

where R is hydrocarbyl containing from 1 to 24 carbons, including mixtures thereof, R' and R" are independently hydrogen, methyl, or ethyl, and n averages 1 to 15.

Examples of such alcohol alkoxylates include glycol ethers such as ethylene glycol monomethyl ether (2-methoxyethanol) and propylene glycol monoethyl ether and the like and ethoxylates derived from mixed $C_2$ to $C_{24}$, preferably $C_2$ to $C_{18}$ and most preferably $C_6$ to $C_{12}$ straight chain alcohols. Suitable ethoxylates where R' and R" are hydrogen and n in the formula averages about 2 to 12, and preferably 3 to 6, are commercially available under the Ethonic ® trademark.

The promoters are used in minor, effective amounts, for example, from about 0.001 to 0.040 moles per mole of α-olefin monomer (0.01 to 4.0 mole percent). In general, the $BF_3$ is used in molar excess to the amount of promoter. This can be accomplished by using a closed reactor and a small $BF_3$ pressure over the reaction mixture. The promoter can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution with temperatures of about 50° C. and above favoring the production of lower oligomers, namely dimer. Preferred reaction temperatures and pressures are about 20° to 65° C. and 5 to 100 psig.

The oligomer mixture from the reaction contains monomer which can be removed by distillation. The monomer has been found to contain mostly less reactive, isomerized material. However, this monomer can be recycled because it will react to form oligomers in the presence of fresh α-olefin monomer. For example, portions of up to about 25 wt % and preferably 5 to 15 wt % recycled monomer based on total monomer can be mixed with fresh monomer. The product mixture can be further separated by distillation to provide one or more product fractions having the desired viscosities for use in various lubricant applications such as drilling, hydraulic or metal working fluids, gear oils and crankcase lubricants.

The alcohol alkoxylates in the presence of $BF_3$, form stable complexes which separate from the product mixture on standing and can be readily recovered and reused. This avoids the $BF_3$ separation and recovery procedures necessary when using, for example, a $BF_3$-butanol complex. In fact, because the alcohol ethoxylates are surfactants, it is preferable to let the catalyst settle from the reaction mixture prior to quenching with base, and especially when using NaOH, in order to avoid the formation of an emulsion.

The oligomer product can be hydrogenated by conventional methods. Supported nickel catalysts are useful. For example, nickel on a kieselguhr support gives good results. Batch or continuous processes can be used. For example, the catalyst can be added to the liquid and stirred under hydrogen pressure or the liquid may be trickled through a fixed bed of the supported catalyst under hydrogen pressure. Hydrogen pressures of about 100 to 1,000 psig at temperatures of about 150° to 300° C. are especially useful.

The invention is further illustrated by, but is not intended to be limited to, the following examples in which the oligomerizations are performed in a three pint stirred reactor consisting of a glass reactor bowl, glass jacket, and a stainless steel top. The reactor is equipped with an air driven magnetic drive stirrer with a marine propeller, a heating/cooling coil and circulating system, dip tube, gas inlet and outlet valves and a pressure relief valve.

EXAMPLES 1-5

1-Decene (600.0 grams, 4.29 moles) and 1.0 mole % based on 1-Decene of Ethonic 610-3, (which is a $C_6$ to $C_{10}$ mixed alcohol ethoxylate having an average of three $+CH_2-CH_2+$ groups), are charged into the reactor which is then assembled and purged with $N_2$ with gentle agitation for 30 minutes. During this time the reactor is brought up to the appropriate reaction temperature by the heating coil circulating system. The reactor is then pressurized ($N_2$) to 20 psig to insure that no leaks exist. After the pressure is relieved the stirring rate is increased and $BF_3$ is introduced into the reactor via a sparge tube located below the surface of the liquid. After a brief (5-10 seconds) purge, the system is pressurized to 10 psig with $BF_3$. The reaction is stopped after the chosen reaction time by venting the $BF_3$ through a 10 wt % NaOH scrubber and quenching with either 5% aqueous NaOH (Examples 2 and 3) or saturated $Na_2SO_4$ (Examples 1, 4 and 5) (50-150 ml). The reactor is purged with dry $N_2$ until all of the $BF_3$ is removed. The polyalphaolefin (PAO)—unreacted decene mixture is washed several times with water, dried over anhydrous $CaCl_2$, and filtered. The product content is determined by gas chromatographic analysis. The reaction times, temperatures and product analysis are given in Table 1.

TABLE 1

| Example | Time (min) | Temperature (°C.) [Max.] | GC Area %[1] Monomer | Dimer | Trimer | Tetramer |
|---|---|---|---|---|---|---|
| 1 | 120 | 20 [28] | 11 | 41 | 42 | 6 |
| 2 | 120 | 32 [39] | 15 | 48 | 32 | 4 |
| 3 | 120 | 45 [50] | 23 | 48 | 20 | 9 |
| 4 | 60 | 45 [52] | 29 | 50 | 19 | 3 |
| 5 | 120 | 80 [86] | 14 | 68 | 16 | 3 |

[1]Where area % ~ weight %

EXAMPLE 6

The process of Example 2 is repeated except at double the amount of alcohol ethoxylate (4 wt %/2 mole %) and quenching is with saturated $Na_2SO_4$. The product distribution in G.C. area % is 9% monomer, 48% dimer, 37% trimer and 6% tetramer.

EXAMPLE 7

The process of Example 3 is repeated except that quenching is with saturated $Na_2SO_4$ and 9.1 wt % of the decene monomer is recycled, considerably isomerized monomer from a previous reaction. The product distribution in G.C. area % is 20% monomer, 52% dimer, 24% trimer and 5% tetramer.

EXAMPLE 8

The process of Example 2 is repeated except that Ethonic 810-6 (2.8 wt %, 1.0 mole %) which is a $C_8$ to $C_{10}$ mixed alcohol ethoxylate having an average of six $+CH_2-CH_2O+$ groups is used as the promoter and quenching is with saturated $Na_2SO_4$. The product distribution in G.C. area % is 24% monomer, 46% dimer, 26% trimer and 4% tetramer.

The dimer fractions from Examples 1, 2 and 3 are separated by distillation and hydrogenated. Their physical properties are reported in Table 2 where the composition is given in G.C. area %.

TABLE 2

| Example | 1 | 2 | 3 |
|---|---|---|---|
| Monomer | — | 0.5 | 0.7 |
| Dimer | 98.9 | 96.7 | 97.9 |
| Trimer | 1.1 | 2.6 | 1.4 |
| Tetramer | — | 0.2 | — |
| $V_{100°C.}$ (cSt) | 1.71 | 1.66 | 1.63 |
| $V_{40°C.}$ (cSt) | 5.22 | 4.99 | — |
| $V_{-40°C.}$ (cSt) | 266.0 | 251.0 | 257.0 |
| Pour Point (°C.) | <−65 | <−65 | <−65 |
| Flash Point (°C.) | 160.0 | 148.0 | 152.0 |

EXAMPLE 9 A-E

This example illustrates the recycle of the promoter/$BF_3$ co-catalyst complex.

1-Decene (600.0 g, 4.29 mol) and Ethonic® 610-3 ethoxylate (11.79 g, 42.9 mmol) are charged into the reactor which is then assembled and purged with N₂ with gentle agitation for 30 minutes; during this time the vessel temperature is brought up to 45° C. The reactor is then pressurized (N₂) to 20 psig to insure that no leaks exist. After the pressure is relieved, the stirring rate is increased and BF₃ is introduced into the reactor via a sparge tube located below the surface of the liquid. After a brief (5–10 seconds) purge, the system is pressurized to 10 psig with BF₃. Periodic samples are collected and quenched with saturated aqueous Na₂SO₄, washed with water (twice), dried over anhydrous CaCl₂, filtered through syringe disk filters, and analyzed by gas chromatography.

After 60 minutes, the BF₃ is purged from the reactor with N₂ for about 30 minutes. The stirring is then stopped to allow the two existing phases to separate (~20 minutes). The upper layer (product 9A) is then drained and washed with 5% aqueous NaOH followed by 2 water washes. The lower layer (co-catalyst) remains in the reactor.

At this point more 1-decene is added and a second reaction initiated by pressurizing the reactor with BF₃ (no additional Ethonic ® 610-3 is added). After 60 minutes the mixture is again purged with N₂, allowed to settle (~20 minutes), and the PAO drained (9B). This procedure is repeated once more to collect a third lot of PAO (9C).

After the third run, the co-catalyst layer is kept in the reactor under an atmosphere of BF₃/N₂. After 20 hours another run (120 minutes) is made to collect a fourth lot of PAO (9D). Again, after an additional 20 hours, a fifth run is made (9E). Results are tabulated in Table 3.

TABLE 3

| Reaction | Time (min) | GC Area % Monomer | Dimer | Trimer | Tetramer |
|---|---|---|---|---|---|
| 9A | 60 | 26 | 50 | 21 | 3 |
| 9B | 60 | 44 | 42 | 12 | 1 |
| 9C | 60 | 46 | 41 | 12 | 1 |
| 9D | 120 | 29 | 54 | 16 | 2 |
| 9E | 120 | 34 | 50 | 14 | 1 |

The results illustrate that the co-catalyst can be easily recycled and remains effective in providing high yields of dimer.

EXAMPLE 10

Example 3 is repeated using 2-methoxyethanol promoter at a concentration of 1 mole % based on monomer. After two hours the G.C. area % product distribution is 8% monomer, 77% dimer, 13% trimer and 2% tetramer or about 85% dimer based on total oligomer product with a conversion to oligomer of over 90%. Repeating the process at double the promoter concentration 2.0 mol % (1.0 wt %) gave about the same result in half the time (one hour instead of two). This example illustrates that an oligomer which is close to a 2 cSt (at 100° C.) viscosity product can be produced by merely removing the monomer.

COMPARISON

A product prepared from 1-Decene monomer using a BF₃ n-butanol catalyst (1.3 mole % n-butanol on monomer) at a reaction temperature of 40° C. and 20 psig BF₃ pressure typically gives a G.C. area % product distribution of about 1% monomer, 2% dimer, 53% trimer, 28% tetramer, 11% pentamer, and 5% hexamer.

What is claimed is:

1. A process for making an α-oligomer comprising contacting a straight-chain α-olefin monomer containing from about 6 to 20 carbon atoms with a catalyst comprising boron trifluoride and alcohol alkoxylate so as to form an oligomer product which is predominantly dimer and trimer of said α-olefin monomer wherein the dimer to trimer ratio is greater than about 1.

2. The process of claim 1 including hydrogenating said product.

3. The process of claim 1 wherein said α-olefin contains 8 to 12 carbon atoms.

4. The process of claim 3 wherein said α-olefin is 1-decene.

5. The process of claim 1 wherein said boron trifluoride is present in an amount of at least about 0.002 mole per mole of α-olefin, the alcohol alkoxylate is present in an amount of from about 0.001 to 0.040 moles per mole of α-olefin and the reaction temperature is in the range of about 0° to 200° C.

6. The process of claim 1 wherein said alcohol alkoxylate has the formula:

$$RO(CHR'-CHR''-O)_nH$$

where R is hydrocarbyl containing from 1 to 24 carbons, including mixtures thereof, R' and R'' are independently hydrogen, methyl, or ethyl, and n averages 1 to 15.

7. The process of claim 1 including the step of separating the catalyst from the product and using said catalyst to contact an α-olefin monomer in the presence of additional BF₃ so as to form an oligomer product.

8. A process for making an α-olefin oligomer comprising contacting a straight chain α-olefin monomer, which contains from about 6 to 20 carbon atoms, with a catalyst comprising boron trifluoride and alcohol alkoxylate so as to produce an α-olefin oligomer reaction product which contains at least about 40 weight percent dimer of said α-olefin monomer based on the total weight of oligomer in said product and which has a dimer to trimer ratio of greater than about 1.

9. A process of claim 8 wherein said boron trifluoride is present in an amount of at least about 0.002 mole per mole of α-olefin, the alcohol alkoxylate is present in an amount of from about 0.001 to 0.040 moles per mole of α-olefin and the reaction temperature is in the range of about 0° C. to 200° C.

10. The process of claim 9 wherein said alcohol alkoxylate has the formula:

$$RO(CHR'-CHR''-O)_nH$$

where R is hydrocarbyl containing from 1 to 24 carbons, including mixtures thereof, R' and R'' are independently hydrogen, methyl, or ethyl, and n averages 1 to 15.

11. The process of claim 10 wherein the alcohol alkoxylate is 2-methoxyethanol.

12. The process of claim 11 wherein the α-olefin is 1-decene and said product contains at least about 50 wt percent dimer based on the total weight of oligomer.

13. The process of claim 11 wherein the α-olefin is 1-decene and said product contains at least about 85 wt percent dimer based on the total weight of oligomer.

14. The process of claim 10 wherein the alcohol alkoxylate is a C₆ to C₁₀ mixed alcohol ethoxylate having an average of six (CH₂—CH₂O) groups.

15. The process of claim 10 wherein the alcohol alkoxylate is a $C_8$ to $C_{10}$ mixed alcohol ethoxylate having an average of six $+CH_2-CH_2O+$ groups.

16. The process of claim 10 including the step of separating the catalyst from the product and using said catalyst to contact an α-olefin monomer in the presence of additional $BF_3$ so as to form an oligomer product.

17. The process of claim 8 wherein a portion of the monomer is recycled monomer.

18. The process of claim 17 wherein the recycled monomer is up to about 25 weight percent of total monomer.

19. The process of claim 1 wherein said oligomer product contains at least about 40 weight percent dimer.

20. The process of claim 19 wherein said oligomer product contains at least about 50 weight percent dimer.

21. The process of claim 20 wherein said oligomer product contains from about 50 to 85 weight percent dimer.

* * * * *

UNITED STATES PATENT AND TRADEMARK OFFICE
CERTIFICATE OF CORRECTION

PATENT NO. : 5,068,487
DATED : November 26, 1991
INVENTOR(S) : Kevin J. Theriot It is certified that error appears in the above-identified patent and that said Letters Patent is hereby corrected as shown below:

COLUMN 6

Claim 14, line 68, reads "an average of six $(CH_2-CH_2O)$ groups." but should read --an average of three $(CH_2-CH_2O)$ groups.--

Signed and Sealed this

Sixth Day of April, 1993

*Attest:*

STEPHEN G. KUNIN

*Attesting Officer*  *Acting Commissioner of Patents and Trademarks*